United States Patent [19]

Hecker

[11] Patent Number: 5,490,630
[45] Date of Patent: Feb. 13, 1996

[54] HAND-HELD AEROSOL DISPENSER FOR THERAPEUTIC LIQUIDS

[75] Inventor: Karl-Heinz Hecker, Aschau, Germany

[73] Assignee: Kendall Medizinische Erzeugnisse GmbH, Neustadt/Donau, Germany

[21] Appl. No.: 232,057

[22] PCT Filed: Oct. 29, 1992

[86] PCT No.: PCT/EP92/02471

§ 371 Date: Apr. 28, 1994

§ 102(e) Date: Apr. 28, 1994

[87] PCT Pub. No.: WO93/08856

PCT Pub. Date: May 13, 1993

[30] Foreign Application Priority Data

Oct. 29, 1991 [DE] Germany .................... 9113446 U

[51] Int. Cl.$^6$ .................... A61M 11/08; A61M 15/00
[52] U.S. Cl. .................... 239/309; 239/338; 239/370; 239/127; 128/200.11; 128/200.18; 128/200.21; 128/203.21
[58] Field of Search .................... 239/338, 309, 239/370, 127; 128/200.18, 200.21, 203.12, 203.21, 203.23, 203.25; 261/78.2; 222/88, 465.1, 325, 158

[56] References Cited

U.S. PATENT DOCUMENTS

| | | | |
|---|---|---|---|
| 3,652,015 | 3/1972 | Beall | 239/370 X |
| 3,771,721 | 11/1973 | Van Amerongen | 128/200.18 |
| 3,857,909 | 12/1974 | Huggins | 261/78.2 X |
| 3,874,379 | 4/1975 | Enfield et al. | 128/200.18 |
| 3,903,216 | 9/1975 | Allan et al. | 261/78.2 |
| 3,903,884 | 9/1975 | Huston et al. | 128/200.18 |
| 3,915,386 | 10/1975 | Vora | 239/338 |
| 4,061,698 | 12/1977 | Thornwald | 261/78.2 |
| 4,149,556 | 4/1979 | Schwabe | 261/78.2 X |
| 4,150,071 | 4/1979 | Pecina | 261/78.2 |
| 4,198,969 | 4/1980 | Virag | 261/78.2 X |
| 4,231,973 | 11/1980 | Young et al. | 239/338 X |
| 4,299,355 | 11/1981 | Häkkenin | 128/200.21 X |
| 4,509,688 | 4/1985 | Gagne et al. | 128/200.21 X |
| 4,595,002 | 6/1986 | Michaels et al. | 128/200.21 |
| 4,620,670 | 11/1986 | Hughes | 128/200.21 X |
| 4,805,609 | 2/1989 | Roberts et al. | 239/338 X |

FOREIGN PATENT DOCUMENTS

| | | |
|---|---|---|
| 38943 | 8/1931 | France . |
| 2437839 | 4/1980 | France . |
| 9011768 | 12/1990 | Germany . |
| 237092 | 7/1945 | Switzerland . |

*Primary Examiner*—Andres Kashnikow
*Assistant Examiner*—Lesley D. Morris
*Attorney, Agent, or Firm*—Jordan and Hamburg

[57] ABSTRACT

A hand-held aerosol dispenser for a therapeutic liquid for inhalation therapy with an atomizer nozzle disposed in a housing for the delivery of compressed air is provided with a detachable reservoir for the liquid. The liquid is aspirated by the Venturi principle through a duct discharging in the region of the atomizer nozzle and atomized into very fine particles using a baffle element opposite the atomizing nozzle. The reservoir, which corresponds in its dimensions to the dimensions of the housing, is detachably accommodated in the lower part of the housing. The duct, discharging in the region of the atomizing nozzle, is elongated downward by a suction nozzle, which passes through an upper opening of the reservoir into the vicinity of the bottom of the reservoir. The reservoir contains sterile water or a mixture of sterile water and drug.

12 Claims, 2 Drawing Sheets

HAND-HELD AEROSOL DISPENSER FOR THERAPEUTIC LIQUIDS

BACKGROUND OF THE INVENTION

The invention relates to a hand-held aerosol dispenser, and more particularly a hand-held aerosol dispenser for a therapeutic liquid used in inhalation therapy.

A hand-held aerosol dispenser for automizing therapeutic liquid, which is held by hand by patients for treatment at home is disclosed, for example, in the German Utility Patent 90 11 768. In the device according to the prior art, a reservoir for the liquid to be atomized is an integral part of the housing. Until now, the patient prepared for the inhalation by mixing an amount of medication and water required for one or several inhalations. The mixture was then transferred to the aerosol dispenser, after which the patient commenced with the inhalation.

Especially with asthmatics suffering an acute attack, this time-consuming preliminary work is beset by the problem that because of the sudden respiratory distress that increases rapidly, the patient panics and, as a result, is often not in a position to carry out the preparations for the necessary inhalation.

As an alternative treatment, an emergency powder inhalation may be used by the asthmatic. However, as a rule, only a medication of a related type is available. Moreover, the dry powder inhalation in most cases exerts a strongly irritating effect on the already damaged bronchia.

Furthermore, simple tap water has been used in the prior art, for moistening the bronchial region as well as for preparing a mixture of water and the drug. Such water may prove unsuitable for inhalation therapy. Although there are usually no complications when such water is used for external and oral applications, the impurities contained in tap water can, in certain instances, lead to serious infections in the lung.

U.S. Pat. No. 3,915,386 discloses a room humidifier, which also works with an atomizing nozzle. Such room humidifiers are used for the purpose of optimizing the room atmosphere in sensitive areas, such as in operating rooms. The known humidifier has a reservoir, which can be screwed into the housing from below and can contain sterilized water. The known apparatus is not suitable for use as a hand-held device, because the reservoir has a capacity of about 1 liter and is also not intended for atomizing a drug mixture, since such use would be inappropriate for room humidification.

OBJECTS AND SUMMARY OF THE INVENTION

It is therefore an object of the invention to develop a hand-held aerosol dispenser of the aforementioned type further, which is ready for use at all times and for which the use of contaminated water is precluded.

Briefly stated, there is provided a hand-held aerosol dispenser available, with which sterile water or a mixture of sterile water and a drug are supplied in a reservoir, which can be removed from the housing. The patient can mix the amount of the drug prescribed by the doctor with the sterile water, in the reservoir. When the reservoir is coupled with the housing, the hand-held aerosol dispenser is ready for use for about 20 inhalations, which normally corresponds to 7 days. Due to the absence of nutrients in the sterile water, the body's own bacteria, which subsequently reach the sterile water through the top of the reservoir, cannot adversely affect the liquid held therein.

In a further embodiment of the present invention, an already pre-mixed drug is pre-filled within the reservoir, so that the patient need only connect the reservoir with the housing, in order to obtain an aerosol dispenser that is ready for use.

A suction nozzle, through which the therapeutic liquid is drawn, and which reaches almost to the bottom of the reservoir, ensures that the reservoir can be emptied almost completely.

According to a further feature of the invention, improved atomizing results and, moreover, particularly with respect to the separation of the small droplets from the larger ones, is achieved by surrounding the atomizing nozzle with a cylindrical separation chamber, which is open at the bottom and disposed within the housing a distance from its side. The separating chamber is connected to the outside air through openings in the cylinder wall and openings in the housing wall. In this way, the mist produced is carried downward as in a chimney. Due to the deflection of the mist stream through about 180°, which then takes place during inhalation, a particularly good separation of the small droplets from the larger droplets is attained which, as a result of the centrifugal force, are flung against the inner wall of the housing and then flow back into the reservoir.

The above, and other objects, features and advantages of the present invention will become apparent from the following description read in conjunction with the accompanying drawings, in which like reference numerals designate the same elements.

DETAILED DESCRIPTION OF THE INVENTION

Figure 1:
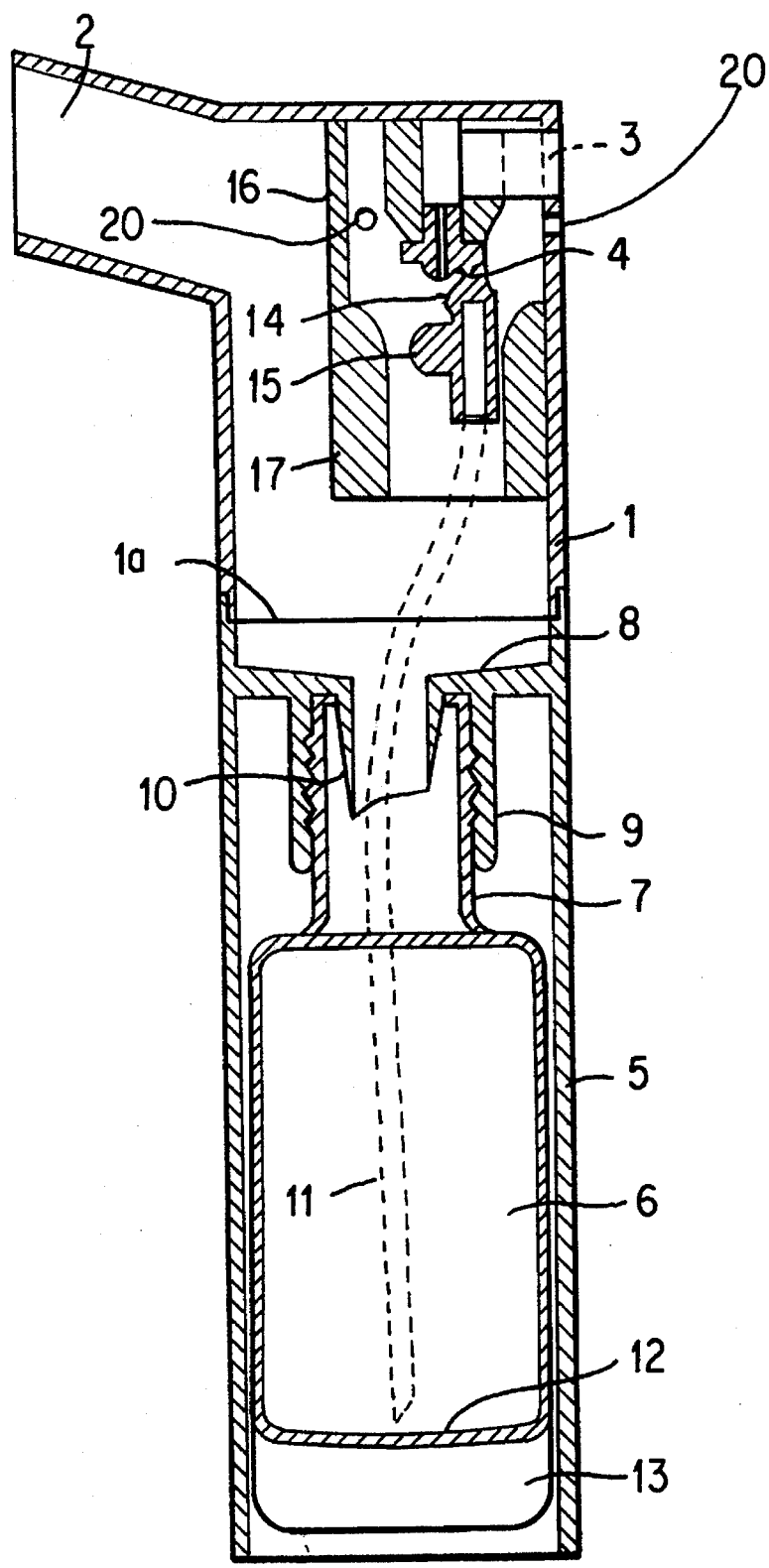
FIG. 1 is a longitudinal sectional view of the hand-held aerosol dispenser.
Figure 2:
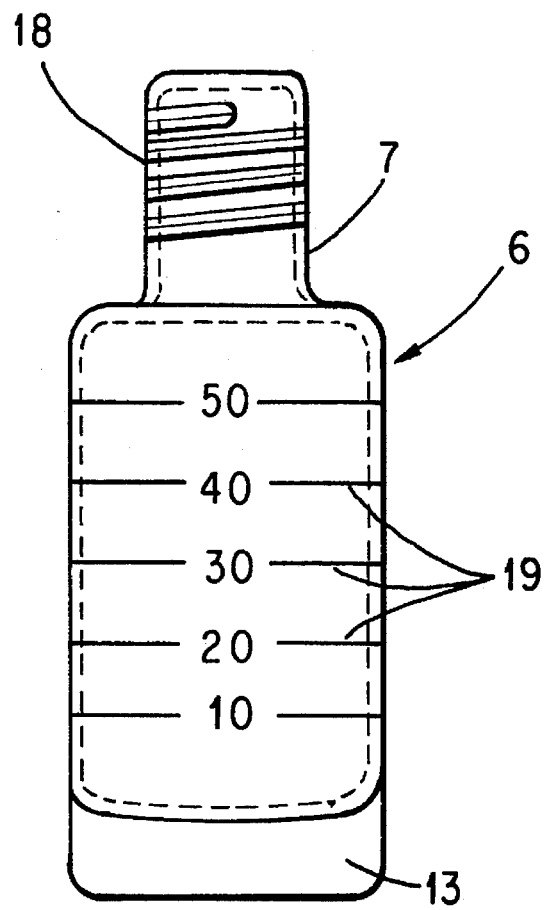
FIG. 2 is a side view of the reservoir.
Figure 3:
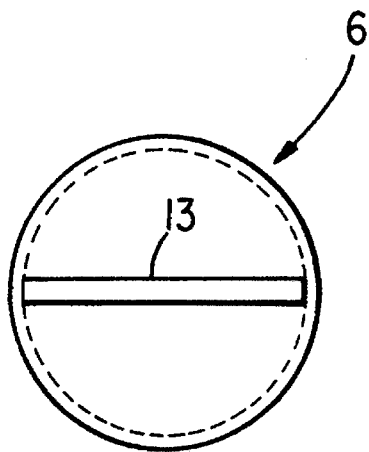
FIG. 3 is a bottom view of the reservoir of FIG. 2.

A housing 1, which is divided along a joint 1a into two parts, includes a mouth piece 2, a compressed air supply line 3 and an atomizing nozzle 4.

The housing 1 has a cylindrical part 5, which protrudes downward and is open at the bottom. A reservoir 6 is disposed within this cylindrical part 5.

The reservoir 6 is detachably connected with the housing 1. A neck part 7 of the reservoir 6 is screwed into connection piece 9 with internal thread, which protrudes downward from a partition 8. Within the connection piece 9, there is a breaker connection piece 10, with which the cover of the reservoir 6 is broken open when the reservoir 6 is screwed in.

The internal diameter of this breaker connection piece 10 is larger than the external diameter of a suction nozzle 11, so that air can enter the reservoir 6 and the larger droplets, which have been separated by the separating apparatus, can also flow back into the reservoir. In order to facilitate this flowing back, the partition 8 is inclined all around to the breaker connection piece 10.

The suction nozzle 11, which is connected at the top and discharges into a suction opening 14, extends almost to the bottom 12 of the reservoir 6, so that the latter can be emptied almost completely. For this purpose, it is advantageous that the bottom 12 of the reservoir 6 slopes downwards all around to a low point.

At its underside, the bottom 12 of the reservoir 6 has a stay 13, which is used as a handle when screwing in the reservoir 6.

In the upper part of the housing 1, there is a device for atomizing the liquid and for separating the small droplets from the larger droplets, which cannot be used. This device comprises the atomizer nozzle 4, to which compressed air is supplied from above over the compressed air line 3. As the compressed air leaves the atomizer nozzle 4, liquid is aspirated at the exhaust opening 14 by the Venturi principle and atomized when the emerging jet of compressed air with the liquid droplets impinges on a baffle element 15.

The device is accommodated within the cylindrical separating chamber 16. This separating chamber 16 is disposed eccentrically within the housing 1 spaced apart from the wall of the housing 1. The interior is in contact with the outside air through openings 20, which are provided in the wall of the separating chamber 16 and in the wall of the housing 1. In this way, under the influence of the reduced pressure occurring in the separating chamber, outside air is aspirated and conducted downward together with the mist as in a chimney. At the place where this mixture is deflected upward and during inhalation at the lower end of the separating chamber, the larger droplets, which are not usable for the inhalation, are flung away and flow back into the reservoir 6.

Within the separating chamber 16, and disposed in its lower part, a thickening 17 with an internal diameter smaller than that of the remaining chamber region is provided, which is rounded off at the top about level with the suction opening 14. The thickening 17 serves to optimize the separation of the small droplets from the larger ones.

Referring now to FIG. 2, reservoir 6 is shown, which is approximately bottle-shaped and the neck part 7 of which is provided with a thread 18.

The reservoir 6 is provided with markings 19 to indicate the level to which it is filled. These markings 19 can be used, for example, when the mixture of sterile water and drug is prepared by the patients themselves. The markings 19 make it easier to prepare particular mixing ratios. Further, they indicate the number of available inhalations remaining in the reservoir. Normally, the reservoir 6 is screwed into the transparent housing before mixing.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

I claim:

1. A hand-held aerosol dispenser for a therapeutic liquid for inhalation therapy, comprising:

a housing including means for detachably connecting with a reservoir, said reservoir for containing said therapeutic liquid therein;

said housing further including a partition disposed therein;

said partition including a connecting piece carried on a lower part thereof, said connecting piece comprising said means for detachably connecting with a reservoir;

a breaker connection piece disposed within said connecting piece;

said breaker connection piece having an external dimension smaller than an internal dimension of said neck part of said reservoir;

means for receiving compressed air including an atomizing nozzle disposed within said housing;

a suction opening disposed proximate said atomizing nozzle, said suction opening communicating with said therapeutic liquid through a suction nozzle having a lower end terminating proximate a bottom of said reservoir when said reservoir is connected to said housing;

a cylindrical separating chamber, open at a bottom thereof, and which surrounds said atomizer nozzle;

said cylindrical separating chamber being spaced apart from an inner surface of said housing;

said cylindrical separating chamber and said housing include openings formed therethrough communicating with outside air; and a mouthpiece for inhaling a mist produced within said housing.

2. The hand-held dispenser according to claim 1, wherein said reservoir is held at least partially within said housing.

3. The hand-held dispenser according to claim 1, wherein said reservoir is screwed into said housing.

4. The hand-held dispenser according to claim 1, wherein said means for detachably connecting with a reservoir includes screw threads carried on said housing for cooperating with screw threads carried on said reservoir.

5. The hand-held dispenser according to claim 1, wherein an inner surface of said bottom of said reservoir slopes inwardly downward to a low point.

6. The hand-held dispenser according to claim 1, wherein said reservoir includes markings indicating a level of said therapeutic liquid within said reservoir.

7. The hand-held dispenser according to claim 1, further comprising:

a cylindrical separating chamber, open at a bottom thereof, and which surrounds said atomizer nozzle;

said cylindrical separating chamber being spaced apart from an inner surface of said housing;

said cylindrical separating chamber and said housing include openings formed therethrough;

an inner wall of said cylindrical separating chamber is provided with a thickening having an inner diameter which is smaller than that of a remainder of said cylindrical separating chamber; and said thickening is rounded off at a top surface thereof.

8. The hand-held dispenser according to claim 7, wherein said top surface of said thickening is disposed about level with said suction opening.

9. The hand-held dispenser according to claim 7, wherein said cylindrical separating chamber is disposed eccentrically within said housing.

10. The hand-held dispenser according to claim 1, wherein:

said housing has a joint above said partition; and said joint divides said housing into an upper part and a lower part.

11. The hand-held dispenser according to claim 10, wherein said breaker connection piece has a lower free end remote from said bottom of said reservoir.

12. A hand-held aerosol dispenser for a therapeutic liquid for inhalation therapy, comprising:

a reservoir for containing said therapeutic liquid therein;

a housing including means for detachably connecting with said reservoir;

means for receiving compressed air including an atomizing nozzle disposed within said housing;

a suction opening disposed proximate said atomizing nozzle, said suction opening communicating with said therapeutic liquid through a suction nozzle having a lower end terminating proximate a bottom of said reservoir when said reservoir is connected to said housing;

a radial stay carried on an outer surface of said bottom of said reservoir; and a mouthpiece for inhaling a mist produced within said housing.

* * * * *